(12) United States Patent
Majeed et al.

(10) Patent No.: US 7,253,324 B1
(45) Date of Patent: Aug. 7, 2007

(54) PROCESS FOR THE SYNTHESIS OF BIOLOGICALLY ACTIVE OXYGENATED COMPOUNDS BY DEALKYLATION OF THE CORRESPONDING ALKYLETHERS

(75) Inventors: Muhammed Majeed, Piscataway, NJ (US); Samuel Manoharan Thomas, Bangalore (IN); Kalyanam Nagabhushanam, Piscataway, NJ (US); Sivaprakash Kurumanghat Balakrishnan, Bangalore (IN); Subbalakshmi Prakash, Piscataway, NJ (US)

(73) Assignee: Sami Labs Limited, Bangalore (IN)

( * ) Notice: Subject to any disclaimer, the term of this patent is extended or adjusted under 35 U.S.C. 154(b) by 0 days.

(21) Appl. No.: 11/626,225

(22) Filed: Jan. 23, 2007

(51) Int. Cl.
   *C07C 37/00* (2006.01)

(52) U.S. Cl. .................................................. 568/805
(58) Field of Classification Search .................. None
   See application file for complete search history.

(56) References Cited

OTHER PUBLICATIONS

Loubinoux et al (Synthesis Communications, "Selective demethylation of Aryl Methyl Ethers" pp. 638-640 1980).*

* cited by examiner

*Primary Examiner*—Johann Richter
*Assistant Examiner*—Kellette Gale

(57) ABSTRACT

Alkoxy aromatic compounds are conveniently dealkylated to the corresponding phenolic compounds by treatment with aluminum chloride/N,N-dimethyl aniline complex. Aromatic poly O-demethylation is a unique feature of this invention. This process is applicable to the manufacture of polyphenols such as Resveratrol, Oxyresveratrol, Gnetol.

7 Claims, No Drawings

US 7,253,324 B1

PROCESS FOR THE SYNTHESIS OF BIOLOGICALLY ACTIVE OXYGENATED COMPOUNDS BY DEALKYLATION OF THE CORRESPONDING ALKYLETHERS

BACKGROUND OF THE INVENTION

Phenolic groups occur ubiquitously in many natural products and also form an important functional group in synthetic organic chemicals. Often times, it is necessary to perform reactions on these molecules containing the phenolic group function. Phenolic —OH groups activate the reactivity of aromatic nucleus towards electrophilic substitution so heavily that selectivity of the reactions is lost many a time. Also, the acidity of the phenolic hydrogens prevents performance of acid-sensitive reactions such as carbanion formation. Hence often times it is necessary to protect the phenolic functions, namely the phenolic —OH group suitably. Benzyl groups have been used extensively for the protection of phenolic groups (Wuts, P G M, Greene's *Protective Groups in Organic Synthesis*, $4^{th}$ edition, John Wiley & Sons, 2007, pages 396-406), their (benzyl group) removal has always been effected by catalytic hydrogenation. The use of catalytic hydrogenation a priori cannot be performed if the molecule contains unsaturation such as carbon-carbon multiple bonds that may get hydrogenated simultaneously. Use of t-butyl groups has been considered. But the installation as well as the removal of t-butyl groups from phenolic substrates is always not very convenient (Wuts, P G M, Greene's *Protective Groups in Organic Synthesis*, $4^{th}$ edition, John Wiley & Sons, 2007, page 396). While installation of t-butyl groups requires isobutylene or an unstable t-butyl halide, their (t-butyl group) removal to release phenolic groups often requires highly acidic conditions. Tetrahydropyranyl (THP) ethers is another choice. However protection of phenolic groups as THP ethers and their subsequent use is a studious operation and introduces additional elements of chirality. This results in, if multiple phenolic groups are present in the substrate, several diasteromers of the product, often complicating analysis and isolation issues. Protection of phenolic groups with acyl moiety is another strategy. However this also is also limited by the liability of acyl groups even in mildly basic conditions.

Phenolic groups can be protected as alkyl ethers. Foremost among them are methyl ethers (Wuts, P G M, Greene's *Protective Groups in Organic Synthesis*, $4^{th}$ edition, John Wiley & Sons, 2007, pages 370-382). Introduction of methyl group onto a phenolic moiety is simple. Common reagents such as methyl iodide, dimethyl sulfate, diazomethane or more recently environmentally acceptable dimethyl carbonate (Perosa, A; Selva, M; Tundo, P & Zordan, F; 2000, Synlett., 272) can be judiciously used to convert phenolic groups to the corresponding methyl ethers. Conversion to other ethers such as ethyl ethers also follows a similar strategy.

Once the phenolic group is protected as an ether, reactions could be performed on the molecule; Finally the ether must be deprotected to release the parent phenol. Several methods have been described in prior art. They suffer from one disadvantage or another.

We describe in this invention an unique method of O-dealkylation

RELATED PRIOR ART

Several reviews have been written on reagents used in O-dealkylation of aromatic ethers including methyl ethers (Weissman, S A & Zewge, D; 2005, *Tetrahedron.*, 61, 7833; Ranu, B C & Bhar, S; 1996, *Org. Prep. Proc. Int.*, 28, 371; Bhatt, M V & Kulkarni, S U; 1983, *Synthesis*, 249). By citing these reviews, we are also including the cited references in them as part of prior art in this field. For example phenolic methyl ethers have deprotected to unmask the phenol using hydrogen halide such as hydrogen iodide or hydrogen bromide under highly acidic conditions. (Meltzer, R I; Lustgarten, D M & Fischman, A, 1957, *J Org Chem.*, 74, 1316; Landini, D; Montanari, F & Rolla, F; 1978, *Synthesis*, 771 for use of HBr with PTC); Highly colored products do form in these reactions. In addition the phenolic compounds react further with the halogen compounds used thus setting a major limitation on this strategy.

Another reagent used is pyridinium chloride. However, invariably high temperatures are employed for the demethylation reaction. Temperatures of reaction near 200° C. are common (For a recent example see Schmid, C R; Beck, C A; Cronin, J S & Staszak, M A; 2004, *Org. Proc. Res. Dev.*, 8, 670) In the cited case the temperature of the demethylation reaction is in the range 185-195° C. Hence sensitive substrates cannot be O-dealkylated using this procedure In the case of Lewis acids, aluminum chloride-N,N-dimethyl or N,N-diethyl aniline has been employed for aromatic O-debenzylation or O-deallylation. (Akiyama, T; Hirofuji, H & Ozaki, S; 1991, *Tetrahedron Lett.*, 1321; (Akiyama, T; Hirofuji, H & Ozaki, S; 1992, *Bull. Chem. Soc. Jpn.*, 65, 1932). No cases of aromatic O-demethylations or have been reported so far. Other Lewis acids such as boron trichloride/boron tribromide etc have been reported. In these cases usually very low temperatures have been employed adding enormously to the inconvenience of performing such reactions in larger industrial levels (Brooks, P R; Wirtz, M C; Vetelino, M G; Rescek, D M; Woodworth, G F; Morgan, P B & Coe, J W; 1999, *J Org Chem.*, 64, 9719; Fujita, M; Qi, G; Verkerk, U. H.; Dzwiniel, T L; McDonald, R & Stryker, J M; 2004, *Org. Lett.*, 6, 2653) In the cited instances temperature of the aromatic O-demethylation reaction was kept near −78° C.

Aromatic O-Demethylations have been carried out with thiolate catalysts. However the use of evil smelling thiols would be a limiting factor for practical applications, thus necessitating the employment of special thiols (Magano, J; Chen, M H, Clark, J D & Nussbaumer, T; 2006, *J Org Chem.*, 71, 7103 and references cited therein)

Another area is in the case of poly aromatic O-demethylation reactions. When a substrate contains more than one aromatic demethoxy group, there are not convenient methods for demethylating all of the —OCH₃ groups present in that substrate. For poly O-demethylation reactions (wherein several aromatic methoxy groups present in a single molecule need to be converted to the corresponding phenolic groups), the methods employed use of pyridinium chloride (for an example of di O-demethylation see, Bachelor, F W; Loman, A A & Snowdon, L R R; 1970, *Can J Chem.*, 48, 1554) or hydrobromic acid (Craig, P N; Nabenhaver, F P; Williams, P M; Macko, E & Toner J; 1952, *J Am Chem Soc.*, 74, 1316). Both suffer from disadvantages described earlier.

In the case of aromatic poly O-demethylation, the reactions are very important since they are applicable to the synthesis of biologically, medically and nutritionally important polyhydroxy stilbenes. By the application of the present invention through the use of aluminum chloride/N,N-dimethyl aniline reagent system (see below) to poly O-demethylation of polymethoxy stilbenes, we have discovered a new, convenient route Resveratrol, Oxyresveratrol, Gnetol by poly O-demethylation of appropriate precursor-stilbene derivatives. Such poly-O-demethylation reactions also form part of our invention.

DESCRIPTION OF THE PRESENT INVENTION

We discovered that aromatic alkyl ethers (aryl alkyl ethers) are cleanly cleaved/removed by treatment with aluminum chloride/N,N-dimethyl aniline in a solvent, hereinafter referred as the "aluminum chloride/N,N-dimethyl aniline reagent" or "aluminum chloride/N,N-dimethyl aniline reagent system"

The alkyl groups present in these aromatic alkyl ethers (aryl alkyl ethers) can be short chain, linear or branched alkyl groups consisting of C1 to C-8 carbons. In several of the following examples we have chosen methyl or ethyl ethers as examples of these aromatic alkyl ethers (aryl alkyl ethers). Since in the practice of organic chemistry, methyl ethers are more easily prepared and handled, many illustrative examples use aromatic methyl ethers. However without loss of generality, our invention covers alkyl groups also.

Also without loss of generality, in stead of N,N-dimethyl aniline, one can also use N,N-diethyl aniline or other mixed amine such as N-methyl-N-isopropyl aniline serving the same end use, namely aromatic O-demethylation. In stead of the phenyl group in N,N-dimethyl aniline component of the reagent, one can, if occasion so demands, other substituted phenyl groups or naphthyl groups. Such variations of this innovation are also covered in this application and representative list is shown below

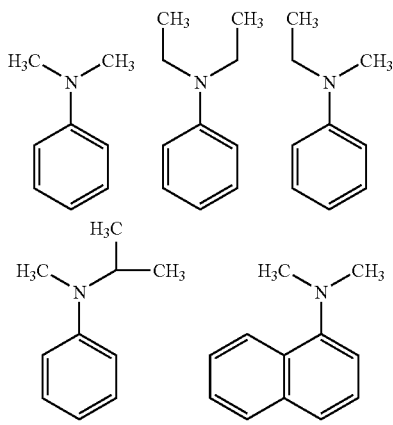

The solvents used can be chosen from chlorinated aliphatic solvents such as methylene chloride, chloroform in addition aromatic solvents such as toluene. Higher boiling solvents such as o-, m or p-xylenes can also be used. Mixed xylenes or mesitylene can also be used advantageously. In certain cases, the amines themselves forming part of aluminum salt-amine reagent system can be used as solvents.

The molar ratio of aluminum chloride to N,N-dimethyl aniline is generally 1:1; The reaction is so general that it allows variations in this ratio also.

It is possible that the reagent system aluminum chloride-N,N-dimethyl aniline type systems is forming an ionic liquid; Such theories not with standing, this reagent system is very effective in aromatic O-dealkylation reaction.

The reaction can be heated depending on the sensitivity of the substrate. General reaction temperatures for the demethylation reaction brought about by aluminum chloride-N,N-dimethyl aniline is in the range 0°-180° C. depending on the substrate and solvent used; The preferred temperature range is 40°-120° C.;

The scope of the demethylation reaction is expansive. Halogens on the aromatic moiety are not disturbed and the methoy group is cleaved cleanly leaving the halogens intact. Examples 2 & 3 illustrate this advantage of the reagent. In this respect, aluminum chloride-N,N-dimethyl aniline system will be superior to the thioalkoxide systems which invariably interfere with the halogens present on the aromatic ring.

Example 4 illustrates another unique advantage of this reagent system wherein an aromatic methoxy is removed leaving an C-allyl group undisturbed. The starting material is methyl chavicol (4-allyl-1-methoxybenzene) which is a cheap and abundantly available natural product. The product p-allylphenol was obtained in very good yields and high purity.

To illustrate further wide scope of application of this reaction, we used p-ethoxy allylbenzene as the substrate as shown in Example 5. This was also cleanly converted to p-allylphenol without incident. Thus the nature of the ether group is not limited to methyl group alone and is inclusive of, and extendible to higher alkyl groups also.

While we extensively used the commonly available N,N-dimethyl aniline in combination with aluminum chloride, we found that N,N-dimethyl aniline can be substituted by 1-(N,N-dimethylamino)-naphthalene with comparable results, thus showing a diverse structure of amino compounds could be used as shown in Example 6.

The methoxy groups can be present not only on a phenyl ring but it could be present on a naphthalene ring system too as shown in Example 7. Thus methoxy groups present on a polycyclic aromatic hydrocarbon are also cleaved by this reagent and such variations are also covered under this invention The aluminum chloride-N,N-dimethyl aniline reagent system, also tolerates the presence of aromatic cyano groups. The cyano groups survive intact while the reagent system cleaves cleanly the aromatic methoxy group to the parent phenolic group. When the starting cyanoaromatic compound contains two methoxy groups, the reagent system offers an interesting possibility of cleaving only one of the two methoxy groups leaving the second methoxy group and the cyano functionality intact as exemplified by Examples 8 & 9 respectively.

In further attempts to elucidate the application of this general aromatic O-demethylation on poly functional molecules, we investigated the aromatic O-demethylation of compounds in which ester functions (methyl ester and ethyl ester) are additionally present. We discovered that this reagent system cleaves cleanly not only the ether-methoxy groups but also the ester-methoxy and ester ethoxy groups also. Examples 10 & 11 illustrate the utility of this reagent under these conditions.

When the substrate molecules contain a ketonic function such as in p-anisylacetopheneone (Example 12) or in p-anisyl cyclopropyl ketone (Example 13), the products identified were the corresponding carboxylic acid with the methoxy groups in tact albeit in low yields.

If aldehydic groups are present as in p-anisaldehyde, no useful products were identified from the reaction.

If nitro groups, as in p-nitroanisole, the substrate was recovered as such. All the reaction products are well characterized with spectral data.

In order to illustrate the practice of this invention in poly O-demethylation of aromatic methoxy groups, we used several methoxylated substrates as mentioned herein and treated them with aluminum chloride-N,N-dimethyl aniline reagent. The examples given are illustrative and are not exhaustive. They serve to prove the generality of the method. They do not limit the scope of this invention.

Stilbene polyphenols belong to an useful category of polyphenols exhibiting diverse pharmacological activities such as antioxidant properties, induction of apoptosis, tyrosinase inhibition etc (Fresco, P; Borges, F; Diniz, C & Marques, M P M; 2006, *Medicinal Research Reviews*, 26, 747). (Roupe, K A; Remsberg, A M; Yanez, J A & Davis N M; 2006, *Current Clinical Pharmacology*, 1, 81). Resveratrol, Oxyresveratrol, Gnetol, Pterostilbene, Rhapontigenin, Piceatannol, Pinosylvin etc all belong to this category. By the application of the synthetic methodology invented in this patent for aromatic O-demethylation, we have been able to demethylate three and four methoxy groups with facility for exemplary synthesis of these stilbene polyphenols.

To illustrate examples of poly O-demethylation of aromatic methoxy groups, we employed aluminum chloride/N,N-dimethyl aniline reagent system to demethylate the substrate 3,4',5-trimethoxystilbene cleanly to Resveratrol. Thus in this process, Example 14, three aromatic methoxy groups have been demethylated to unmask three phenolic groups.

In yet another Example 15, we demonstrate the demethylation of four aromatic methoxy groups in a new synthesis leading to Oxyresveratrol.

In yet another demonstration of this powerful poly aromatic O-demethylation reaction with the use of aluminum chloride/N,N-dimethyl aniline reagent, we exemplify in Example 16, the demethylation of again four aromatic methoxy groups to unmask the corresponding phenols in the first synthesis of Gnetol By adjusting the moles of aluminum-chloride/N,N-dimethyl aniline reagent with respect to the number of alkoxy groups, say, methoxy groups present, one can deakylate, say, demethylate, compounds with two to eight methoxy groups. Alkoxy groups such as benzyloxy are more easily deakylated than methoxy groups. Hence the reagent performs a debenzylation, sometimes at a lower temperature.

Thus the reagent system aluminum chloride/N,N-dimethyl aniline demonstrates a preference to debenzylate a —O-benzyl group (benzyloxy) in preference to a O-methyl (methoxy) group. We utilize this property of this reagent in a new synthesis leading to Rhapontigenin in Example 17

General illustrative procedures are given again to only to exemplify the practice of the novel process but they do not limit the scope of variations that are possible. The examples are thus illustrative and are not exhaustive.

EXAMPLE 1

General Procedure for O-Demethylation of Model substrates: The following typical procedure involving 4-fluoroanisole is applicable for all other similar substrates. N,N-Dimethylaniline (9.6 g, 0.079 mol) was taken in a 100 mL round bottomed flask under dry nitrogen atmosphere. Anhydrous aluminum chloride (10.6 g, 0.080 mol) was added slowly with stirring at room temperature. After the addition of aluminium chloride is over, dry toluene (5 mL) was added to this mixture and stirred for 10-15 min. 4-Fluoroanisole (5 g, 0.040 mol) dissolved in toluene (15 mL) was dropped into this mixture with stirring and the mixture heated to 100-110° C., and maintained at this temperature for 2-3 h. This was then cooled to room temperature, and slowly dropped into ice water (50 mL) with stirring, followed by acidification with hydrochloric acid to pH=1-2. The toluene layer was separated, and the aq. layer extracted with toluene (2×15 mL). The toluene extracts combined, and extracted with 10% aq. sodium hydroxide (3×30 mL). The basic aq. phase was acidified with hydrochloric acid and extracted with toluene (3×30 mL), which was dried over anhydrous sodium sulfate, filtered, and the solvent stripped off under vacuum to get the pure product 4-fluorophenol (3.6 g) as a liquid.

EXAMPLE 2

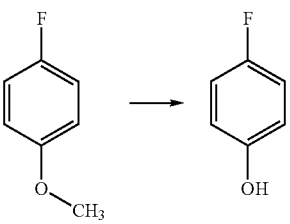

The general procedure adopted for this conversion is described in Example 1. The yield of the product was 80%; The product p-fluorophenol was characterized by proton NMR (Solvent CDCl$_3$, Proton 300 MHz): δ 5.98 (s, 1H), 6.77-6.83 (m, 2H), 6.90-6.96 (m, 2H).

EXAMPLE 3

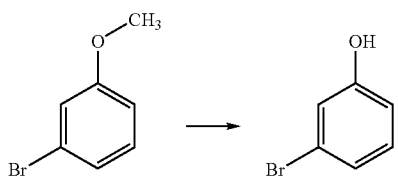

The general procedure adopted for this conversion is described in Example 1. The yield of the product was 65%; The product m-bromophenol was characterized by proton NMR (Solvent CDCl$_3$; Proton 300 MHz): δ 6.12 (br s, 1H), 6.77-6.81 (m, 1H), 7.04 (d, J=1.8 Hz, 1H), 7.09-7.14(m, 2H).

EXAMPLE 4

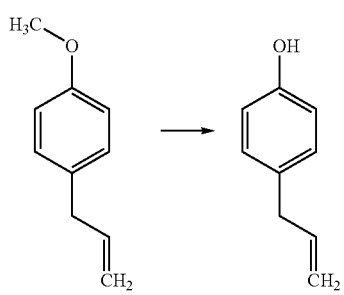

The general procedure adopted for this conversion is described in Example 1. The yield of the product was 81%; The product p-allylphenol was characterized by proton NMR and carbon NMR (Solvent CDCl$_3$, 300 MHz proton): δ 3.28 (d, J=6.9 Hz, 2H), 5.01-5.07 (m, 2H), 5.85-5.98 (m, 1H), 6.23 (br d, 1H, —OH), 6.74-6.78 (m, 2H), 6.99-7.03 (m, 2H).

$^{13}$C NMR(75 MHz, CDCl$_3$): δ 39.65, 115.71, 130.12, 132.77, 138.16, 153.70.

EXAMPLE 5

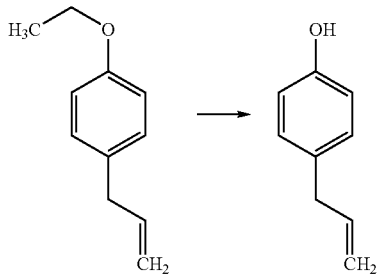

The general procedure adopted for this conversion is described in Example 1. The yield of the product was 80%; The product p-allylphenol was characterized by proton NMR and carbon NMR and was comparable to the data obtained in Example 4

EXAMPLE 6

The general procedure adopted for this conversion is described in Example 1 except that 1-(N,N-dimethylamino)-naphthalene was used in place of N,N-dimethylaniline. The yield of the product was 80%; The product p-allylphenol was characterized by proton NMR and carbon NMR and was comparable to the data obtained in Example 4.

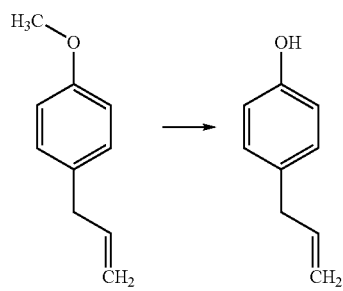

EXAMPLE 7

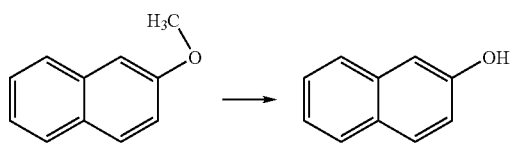

The general procedure adopted for this conversion is described in Example 1. The yield of the product was 85%; The product β-naphthol was characterized by proton NMR
(Solvent CDCl$_3$, 300 MHz Proton) δ 5.00 (br s, 1H, —OH), 7.09-7.16 (m, 2H), 7.31-7.36 (m, 1H), 7.41-7.46 (m, 1H), 7.69 (d, J=9.0 Hz, 1H), 7.74-7.79 (m, 2H).

EXAMPLE 8

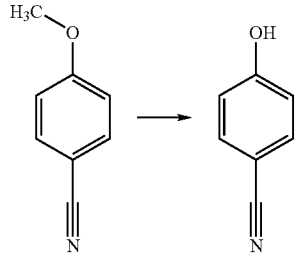

The general procedure adopted for this conversion is described in Example 1. The yield of the product was 50%; The product p-cyanophenol was characterized by proton NMR and carbon NMR
(Solvent CDCl$_3$, 300 MHz Proton): δ 6.10 (br s, 1H, —OH), 6.89-6.94 (m, 2H), 7.53-7.58 (m, 2H).

$^{13}$C NMR(75 MHz, CDCl$_3$): δ 103.63, 116.37, 119.18, 134.32, 159.74.

EXAMPLE 9

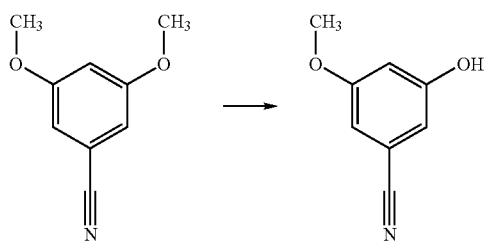

The general procedure adopted for this conversion is described in Example 1. The yield of the product was 70%; The product 3-cyano-5-methoxy phenol was characterized by proton NMR and carbon NMR
(Solvent Acetone-d$_6$, 300 MHz Proton): δ 3.78 (s, 3H), 6.63 (t, J=2.4 Hz, 1H), 6.68-6.71 (m, 2H).

$^{13}$C NMR(75 MHz, Acetone-d$_6$): 56.06, 107.39, 109.48, 112.11, 114.18, 119.28, 159.99, 162.34.

EXAMPLE 10

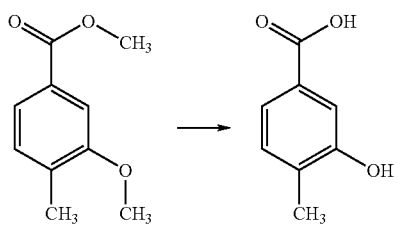

The general procedure adopted for this conversion is described in Example 1. The yield of the product was 90%; The product 3-hydroxy-4-methyl benzoic acid was characterized by NMR conclusively (Solvent DMSO-$d_6$, 300 MHz Proton): δ 2.17 (s, 3H), 7.17 (d, J=7.8 Hz, 1H), 7.31 (dd, J=8.1 Hz, 1.5 Hz, 1H), 7.39 (d, J=1.5 Hz, 1H), 9.68 (s, 1H, —OH), 12.7 (br s, 1H, —COOH).

EXAMPLE 11

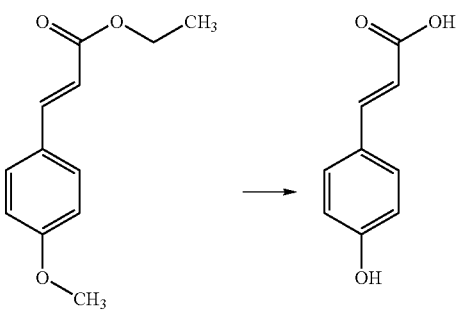

The general procedure adopted for this conversion is described in Example 1. The yield of the product was 75%; The product p-hydroxy-trans-cinnamic acid was characterized by NMR conclusively (Solvent DMSO-$d_6$, 300 MHz Proton): δ 6.29 (d, 2H, J=16.2 Hz), 6.79 (d, 2H, J=8.4 Hz), 7.50 (d, 1H, J=15.9 Hz), 7.52 (d, 2H, J=8.7 Hz), 10.00 (br s, 1H, —OH), 12.20 (br s, 1H, —COOH).

EXAMPLE 12

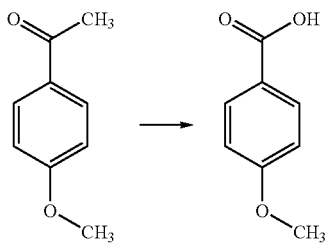

The general procedure adopted for this conversion is described in Example 1. The yield of the product was 15%; The product p-anisic acid was characterized by NMR conclusively (Solvent CDCl$_3$, 300 MHz proton): δ 3.88 (s, 3H), 6.96 (d, J=8.7 Hz, 2H), 8.08 (d, J=8.7 Hz, 2H)

EXAMPLE 13

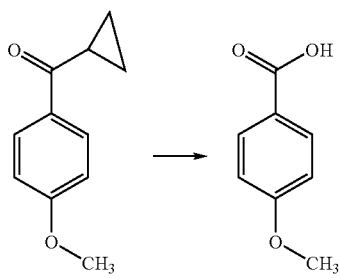

The general procedure adopted for this conversion is described in Example 1. The yield of the product was 5%; The product p-anisic acid was characterized by NMR conclusively NMR and other physical data were the same as that obtained for Example 12

EXAMPLE 14

General procedure for the preparation of Stilbenols: Poly methoxystilbenes were prepared by Emmons-Horner coupling of the corresponding methoxybenzyl phosphonate with methoxyaryl aldehyde. Poly methoxylstilbenes were demethylated using a general procedure. The following procedure involving 3,4',5-trimethoxystilbene is applicable to all similar substrates. N,N-Dimethylaniline (27 g, 0.223 mol) was taken in a 250 mL round bottomed flask under dry nitrogen atmosphere. Anhydrous aluminium chloride (30 g, 0.225 mol) was added slowly with stirring. Dry toluene (25 mL) was added and stirred for 10 min. This was heated to 70-80° C. 3,4',5-tirmethoxystilbene (10 g, 0.037 mol) dissolved in toluene (50 mL) was dropped into the reaction mixture over a period of 5-10 min. The reaction mixture was stirred at 70-80° C. for 2 h. This was cooled to room temperature and dropped into ice water (100 mL) slowly with stirring. Toluene layer was separated. The aq. layer was acidified with 10% hydrochloric acid, and extracted with ethyl acetate (3×100 mL), which was dried over anhy. sodium sulfate, filtered, and the solvents stripped off under vacuum to get the crude resveratrol. This was purified by column chromatography on silica gel using ethyl acetate-hexane as eluent to get pure resveratrol (5.9 g, 70% yield) as white solid.

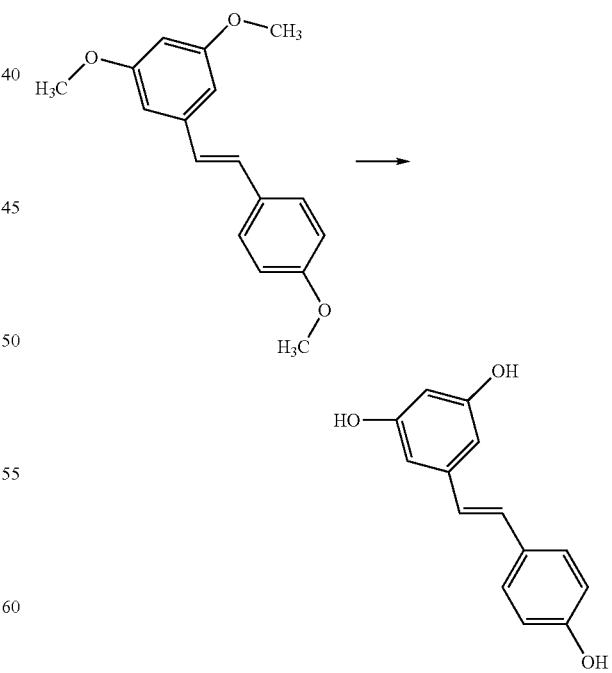

The physical and spectral data for the starting material 3,4',5-trimethoxystilbene:

Mpt: 42.0-44.0° C.

(Solvent CDCl$_3$, 300 MHz proton):δ 3.83 (s, 6H), 3.86 (s, 3H), 6.39 (t, J=2.4 Hz, 1H), 6.66 (d, J=2.4 Hz, 2H), 6.88-6.94 (m, 3H), 7.05 (d, J=16.2 Hz, 1H), 7.46 (d, J=9.0 Hz, 2H)

$^{13}$C NMR(75 MHz, CDCl$_3$): δ 55.56, 55.59, 99.83, 104.55, 114.38, 126.78, 128.06, 128.97, 130.14, 139.93, 159.63, 161.20

LC-MS: m/e 271 (M$^+$+1)

The physical and spectral data for the product Resveratrol:

Mpt: 265.5-267.9° C.

(Solvent Acetone-d$_6$, 300 MHz Proton): δ 6.28 (t, J=2.1 Hz, 1H), 6.55 (d, J=2.1 Hz, 2H), 6.83-6.92 (m, 3H), 7.03 (d, J=16.5 Hz, 1H), 7.43 (d, J=8.7 Hz, 2H), 8.3 (br s, 3H, —OH).

$^{13}$C NMR (75 MHz, Acetone-d$_6$): δ 102.60, 105.62, 116.38, 126.75, 128.72, 129.07, 129.88, 140.86, 158.14, 159.54).

LC-MS: m/e 227 (M$^+$−1).

EXAMPLE 15

For the synthesis of Oxyresveratrol (65% yield) by poly O-demethylation of 2,3',4,5'-tetramethoxy-trans-stilbene, similar procedure as described in Example 14 was adopted The physical and spectral data for the starting material 2,3',4,5'-tetramethoxy-trans-stilbene:

Mpt: 126.7-131.6° C.

(Solvent CDCl$_3$, 300 MHz proton): δ 3.84 (s, 9H), 3.87 (s, 3H), 6.38 (t, J=2.4 Hz, 1H), 6.48 (d, J=2.1 Hz, 1H), 6.52 (dd, J=8.4 Hz, 2.7 Hz, 1H), 6.69 (d, J=2.1 Hz, 2H), 6.96 (d, J=16.2 Hz, 1H), 7.39 (d, J=16.5 Hz, 1H), 7.51 (d, J=8.4 Hz, 1H).

$^{13}$C NMR(75 MHz, CDCl$_3$): δ 55.60, 55.64, 55.74, 98.67, 99.61, 104.57, 105.19, 119.49, 124.05, 127.17, 127.59, 140.61, 158.32, 160.86, 161.12

LC-MS: m/e 301 (M$^+$+1).

The physical and spectral data for the product Oxyesveratrol:

Mpt: 204.0-207.5° C. (Lit. 203-205° C.)

(Solvent Acetone-d$_6$, 300 MHz Proton): δ 6.24 (t, J=2.4 Hz, 1H), 6.38 (dd, J=8.4 Hz, 2.1 Hz, 1H), 6.52 (d, J=2.1 Hz, 2H), 6.89 (d, J=16.5 Hz, 1H), 7.34 (d, J=16.5 Hz, 1H), 7.41 (d, J=8.7 Hz, 1H), 8.3 (br s, 4H, —OH)

$^{13}$C NMR (75 MHz, Acetone-d$_6$): δ 102.25, 103.53, 105.42, 108.41, 117.21, 124.31, 126.23, 128.24, 141.65, 156.90, 159.10, 159.54.

LC-MS: m/e 245 (M$^+$+1).

EXAMPLE 16

For the synthesis of Gnetol (65% yield) by poly O-demethylation of 2,3',5',6-tetramethoxy-trans-stilbene, similar procedure as described in Example 14 was adopted The physical and spectral data for the starting material 2,3',5',6-tetramethoxy-trans-stilbene:

Mpt: 87.2-89.5° C.

(Solvent CDCl$_3$, 300 MHz proton): δ 3.83 (s, 6H), 3.89 (s, 6H), 6.37 (t, J=2.1 Hz, 1H), 6.59 (d, J=8.1 Hz, 2H), 6.70 (d, J=2.4 Hz, 2H), 7.17 (t, J=8.4 Hz, 1H), 7.40-7.53 (AB q, J=16.5 Hz, 2H).

$^{13}$C NMR(75 MHz, CDCl$_3$): δ 55.35, 55.79, 99.32, 103.91, 104.44, 114.48, 120.43, 128.23, 132.25, 141.40, 158.63, 160.77

LC-MS: m/e 301 (M$^+$+1).

The physical and spectral properties of the product Gnetol:

Mpt: 245.4-247.2° C.

(Solvent Acetone-d$_6$, 300 MHz proton): δ 6.25 (t, J=2.1 Hz, 6.44 (d, J=8.1 Hz, 2H), 6.54 (d, J=2.1 Hz, 2H), 6.87 (t, J=7.8 Hz, 1H), 7.43-7.59 (AB q, J=16.8 Hz), 8.17 (br s, 2H, —OH), 8.63 (br s, 2H, —OH).

$^{13}$C NMR (75 MHz, Acetone-d$_6$): δ 102.32, 105.49, 108.04, 112.86, 121.36, 128.76, 132.01, 142.59, 157.61, 159.52.

LC-MS: m/e 243 (M$^+$−1).

EXAMPLE 17

For the synthesis of Pterostilbene (70% yield) by mono O-debenzylation of 4-benzyloxy-3',5'-dimethoxy-trans-stilbene, similar procedure as described in Example 14 was adopted.

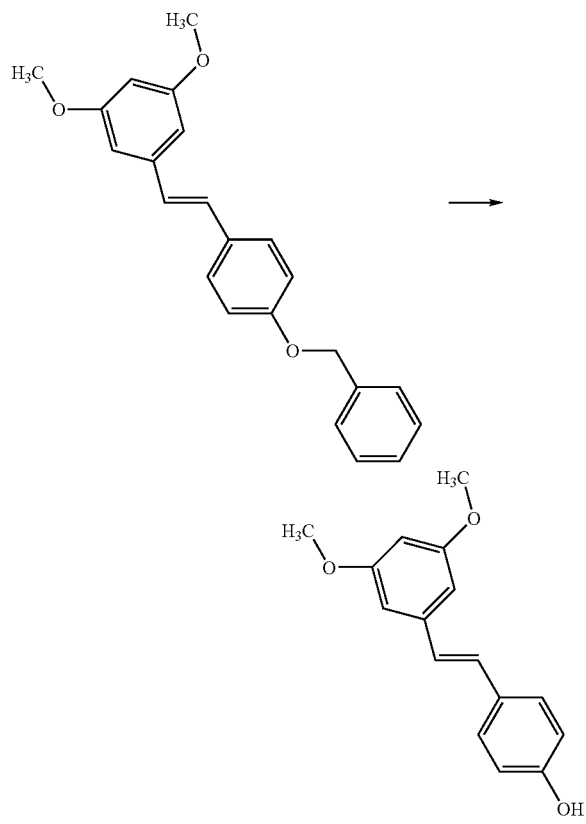

The physical and spectral data for the starting material 4-benzyloxy-3',5'-dimethoxy-trans-stilbene MPt: 106.0-108.0° C.

(Solvent CDCl$_3$, 300 MHz proton): δ 3.83 (s, 6H), 5.09 (s, 2H), 6.38 (t, J=2.1 Hz, 1H), 6.65 (d, J=2.1 Hz, 2H), 6.91 (d, J=16.2 Hz, 1H), 6.97 (d, J=8.7 Hz, 2H), 7.05 (d, J=16.5 Hz, 1H), 7.33-7.47 (m, 7H).

$^{13}$C NMR(75 MHz, CDCl$_3$): δ 55.35, 70.00, 99.56, 104.26, 115.03, 126.63, 127.49, 127.80, 128.02, 128.61, 128.66, 130.10, 136.80, 139.62, 158.54, 160.90.

LC-MS: m/e 347 (M$^+$+1).

Elemental analysis: C 79.11% (requires 79.74%), H 6.40% (requires 6.40%).

The physical and spectral data for the product Pterostilbene

Mpt: 68.0-70.0° C.

(Solvent Acetone-d$_6$, 300 MHz Proton): δ 3.80 (s, 6H), 6.39 (t, J=2.1 Hz, 1H), 6.74 (d, J=2.4 Hz, 2H), 6.86-6.89 (m, 2H), 6.99 (d, J=16.5 Hz, 1H), 7.19 (d, J=16.5 Hz, 1H), 7.44-7.47 (m, 2H), 8.60 (br s, 1H, —OH).

$^{13}$C NMR (75 MHz, Acetone-d$_6$): δ 55.49, 100.01, 104.89, 116.37, 126.48, 128.77, 129.68, 129.76, 140.78, 158.17, 161.96.

LC-MS: m/e 255 (M$^+$-1).

Elemental analysis: C 75.06% (requires 74.98%), H 6.35% (requires 6.29%).

What is claimed is:

1. A process of preparing phenolic product by aromatic O-dealkylation consisting of treating alkoxy-aromatic compound with aluminum salt-amine reagent up to temperature of 120° C. optionally in a solvent for up to 8 hrs, hydrolyzing the reaction mixture with water, acidification and extraction of the phenolic product.

2. A process for preparing phenolic products as claimed in claim 1 wherein the alkoxy group in the alkoxy-aromatic compound is chosen from linear and branched alkyl groups containing C1 to C8 carbons.

3. A process for preparing the phenolic product as claimed in claim 1 wherein the alkoxy-aromatic compound contains, in addition to alkoxy functionality, additional functionalities chosen from bromine, chlorine, ester, cyano, cis-carbon-carbon double bonds, trans-carbon-carbon double bonds, allyl and carbon-carbon triple bonds.

4. A process for preparing the phenolic product as claimed in claim 1 wherein aluminum salt is chosen among aluminum chloride, aluminum bromide.

5. A process for preparing the phenolic product as claimed in claim 1 wherein the amine component of aluminum salt-amine reagent is chosen from N,N-dimethylaniline, N-methyl-N-ethyl aniline, N,N-diethyl aniline, N-methyl-N-isopropyl aniline, 1-N,N-dimethylnaphthalene, 2-N,N-dimethylnaphthalene.

6. A process for preparing the phenolic product as claimed in claim 1 wherein the solvent used is chosen from chlorinated solvents such as methylene chloride, chloroform, ethylenedichloride or aromatic solvents such as benzene, toluene, xylenes, mesitylene or amine solvents chosen from N,N-dimethylaniline, N-methyl-N-ethyl aniline, N,N-diethyl aniline, N-methyl-N-isopropyl aniline, 1-N,N-dimethylnaphthalene, 2-N,N-dimethylnaphthalene.

7. A process for preparing the phenolic product as claimed in claim 1 wherein the aromatic alkoxy compound can contain up to eight alkoxy groups.

* * * * *